United States Patent
Ogata et al.

(10) Patent No.: US 6,277,834 B1
(45) Date of Patent: Aug. 21, 2001

(54) AGENTS FOR RELIEVING SIDE EFFECTS OF ADRENAL CORTEX HORMONE

(75) Inventors: Kazumi Ogata, Osaka; Takahiro Sakaue, Hyogo; Masahito Iemura, Kyoto, all of (JP)

(73) Assignee: Senju Pharmaceutical Co. Ltd., Osaka (JP)

( * ) Notice: Subject to any disclaimer, the term of this patent is extended or adjusted under 35 U.S.C. 154(b) by 0 days.

(21) Appl. No.: 09/719,384

(22) PCT Filed: Jun. 4, 1999

(86) PCT No.: PCT/JP99/03025
§ 371 Date: Dec. 11, 2000
§ 102(e) Date: Dec. 11, 2000

(87) PCT Pub. No.: WO99/65498
PCT Pub. Date: Dec. 23, 1999

(30) Foreign Application Priority Data

Jun. 19, 1998 (JP) .................................. 10-173207

(51) Int. Cl.[7] ...................... A61K 31/665; A61K 31/355; A61K 31/34
(52) U.S. Cl. ........................... 514/100; 514/458; 514/474
(58) Field of Search .................................. 514/100, 458, 514/474

(56) References Cited

U.S. PATENT DOCUMENTS

| | | |
|---|---|---|
| 4,564,686 | 1/1986 | Ogata . |
| 4,888,329 | 12/1989 | Ogata et al. . |
| 4,914,197 | 4/1990 | Yamamoto et al. . |
| 4,948,786 | 8/1990 | Shimamoto et al. . |

FOREIGN PATENT DOCUMENTS

| | | |
|---|---|---|
| 62-145019 | 6/1987 | (JP) . |
| 62-205091 | 9/1987 | (JP) . |
| 63-270626 | 11/1988 | (JP) . |
| 1-27044 | 5/1989 | (JP) . |
| 2-111722 | 4/1990 | (JP) . |
| 2-44478 | 10/1990 | (JP) . |
| 5-23274 | 4/1993 | (JP) . |
| 9-194376 | 7/1997 | (JP) . |

OTHER PUBLICATIONS

Yamamoto, Abstract of Japanese Patent document No. 62–145019, 1987.*
Kazuo et al., Patent Abstracts of Japan Pub. No. 09194376, 1997.*
International Search Report of PCT/JP99/03025 (1999).

* cited by examiner

*Primary Examiner*—Raymond Henley, III
(74) *Attorney, Agent, or Firm*—Merchant & Gould P.C.

(57) ABSTRACT

A medicament for reducing side effects of adrenocortical hormones comprising a phosphodiester compound of the following formula or a pharmacologically acceptable salt thereof

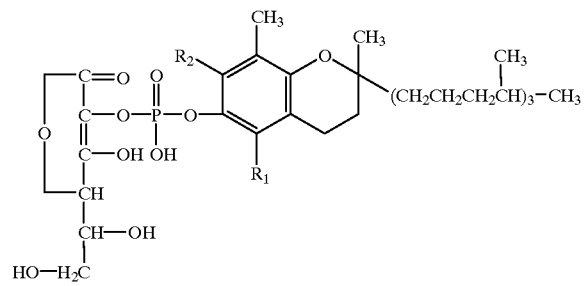

wherein $R_1$ and $R_2$ are the same or different and each denotes hydrogen or methyl.

8 Claims, No Drawings

AGENTS FOR RELIEVING SIDE EFFECTS OF ADRENAL CORTEX HORMONE

This is a 371 of PCT/JP99/03025 filed Jun. 4, 1999.

TECHNICAL FIELD

The present invention relates to a useful medicament for reducing side effects of adrenocortical hormones. More specifically, the present invention relates to a medicament for reducing side effects of adrenocortical hormones which medicament comprises a certain phosphodiester compound constructed from ascorbic acid and tocopherol or a pharmacologically acceptable salt of the compound.

BACKGROUND ART

It is known that adrenocortical hormones, though not having a direct inhibitory effect on phospholipase $A_2$, secondarily exhibits anti-inflammatory effects by inducing production of an anti-inflammatory protein within the cells. However, there is a problem of great clinical importance that an extended use of adrenocortical hormones at high doses causes serious side effects including reduction of glucose tolerance, aggravation of infections, delayed healing of wounds, formation of steroid cataract and induction of glaucoma. Thus, to separate the side effects of adrenocortical hormones from their therapeutic effects is highly desired.

In order to separate the side effects from the therapeutic effects, which are both aspects of the adrenocortical hormonal effects, therefore, agents with adrenocortical hormonal effects must not be overdosed. It is thus considered important to find an adjuvant molecule that can augment adrenocortical hormonal effects, in particular, an adjuvant molecule that can augment adrenocortical hormones-mediated gene expression.

No agent, however, has been known so far to serve as as an adjuvant molecule that is safe and capable of augmenting adrenocortical hormones-mediated gene expression, and there has been a need for an agent that can augment adrenocortical hormonal effects.

Thus, a study was carried out that was directed to reducing the side effects of adrenocortical hormones by combining them with another, adjuvant molecule, thereby allowing to lower the concentration of adrenocortical hormones. The study revealed that a certain group of phosphodiester compounds were capable of augmenting adrenocortical hormonal effects (Japanese Unexamined Patent Publication No. H09-194376).

Upon the above background, however, the present inventors, from a different viewpoint, pursued a study in search of an agent that can directly reduce the side effects of adrenocortical hormones not by reducing their dose (or their concentration in a preparation). In the process, the above phosphodiester compounds were further studied on their interaction with adrenocortical hormones. As a result, it was surprisingly found by the present inventors that those phosphodiester compounds and adrenocortical hormones, when concurrently administered, exhibit a synergism of the anti-inflammatory effects of the respective agents, as opposed to simple addition of their effects. At the same time, it was also unexpectedly found that the side effects of the adrenocortical hormones were directly and remarkably reduced. The present invention was made upon this findings.

DISCLOSURE OF INVENTION

The present invention relates to:

(1) a medicament for reducing side effects of adrenocortical hormones comprising a phosphodiester compound of the following formula or a pharmacologically acceptable salt thereof

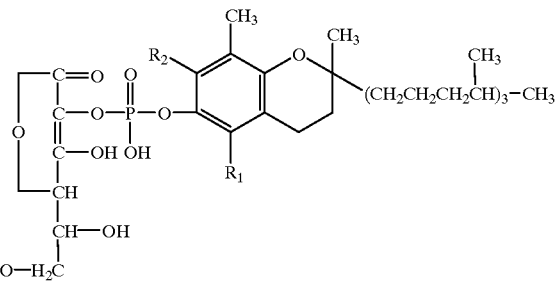

wherein $R_1$ and $R_2$ are the same or different and each denotes hydrogen or methyl (hereinafter referred to as "the present compound"), (2) the medicament for reducing side effects of adrenocortical hormones according to (1) above, wherein the ratio of doses or concentrations in a preparation is 1 mg–100 mg of the phosphodiester compound or a pharmacologically acceptable salt thereof to 1 mg of an adrenocortical hormone, (3) the medicament for reducing side effects of adrenocortical hormones according to (1) or (2) above, wherein the adrenocortical hormone is a compound selected from the group consisting of betamethasone valerate, hydrocortisone, sodium dexamethasone metasulfobenzoate, triamcinolone acetonide, alclometasone propionate, and fluocinolone acetonide, and (4) the medicament for reducing side effects of adrenocortical hormones according to (1) to (3) above, wherein the preparation form thereof is ointment or eye drops.

DETAILED DESCRIPTION OF THE INVENTION

The medicament for reducing side effects of adrenocortical hormones of the present invention can be used as a medicament for reducing side effects of adrenocortical hormones, which have a wide variety of effects including, e.g., antiinflammatory effect and adrenal cortex dysfunction treatment effect. Examples of adrenocortical hormones include, but are not limited to, betamethasone valerate, hydrocortisone, sodium dexamethasone metasulfobenzoate, triamcinolone acetonide, alclometasone propionate, and fluocinolone acetonide.

The present compound used for a medicament for reducing side effects of adrenocortical hormones can be synthesized by or according to the method described in, e.g., Japanese Patent Publication No. H02-44478 or Japanese Unexamined Patent Publication No. S62-205091.

A variety of uses are already known for the present compound used for a medicament for reducing side effects of adrenocortical hormones, including uses as anticataract medicaments, medicaments for prevention and treatment of climacteric disturbance, cosmetics having skin-beautifying effect [Japanese Patent Publication No. H02-44478], antiulcer medicaments [Japanese Unexamined Patent Publication No. S63-270626], and medicaments for prevention and treatment of ischemic disorders of organs [Japanese Unexamined Patent Publication No. H02-111722].

In addition, the present compound is known to directly inhibit an enzyme, phospholipase $A_2$, to thereby exhibit anti-inflammatory effects (Japanese Patent Publication Nos. H01-27044 and H05-23274). As noted above, a further use is also known for the present compound as a medicament for augmenting adrenocortical hormonal effects (Japanese Unexamined Patent Publication No. H09-194376). However, this Japanese Unexamined Patent Publication has as its objective to reduce the side effects of adrenocortical hormones by lowering their doses (or their concentration in a preparation) by combining them with another, adjuvant molecule, and it does not describe a method of directly reducing the side effects of adrenocortical hormones not by reducing their dose (or their concentration in a preparation).

In contrast, the present inventors surprisingly found that those two compounds, when concurrently administered, exhibit synergism of the antiinflammatory effects of the respective agents as opposed to simple addition of their effects and simultaneously found unexpectedly that the side effects of the adrenocortical hormones are directly reduced remarkably without requiring to lower their dose (or their concentration in a preparation). No agent has been known before that can directly and remarkably reduce the side effects of adrenocortical hormones without altering the doses (or the concentration in a preparation) of adrenocortical hormones, as opposed to reducing their side effect by lowering their doses (or their concentration in a preparation) by combining them with another, adjuvant molecule. Thus, the invention is an epoch-making discovery.

For the purpose of the present invention, the present compound used for a medicament for reducing side effects of adrenocortical hormones may be used in its free form or in the form of a pharmacologically acceptable salt thereof. Examples of such pharmacologically acceptable salts include, but are not limited to, alkaline metal salts such as sodium salt, potassium salt and the like, and alkaline earth metal salts such as calcium salt, magnesium salt and the like. Other salts may be used insofar as they are pharmacologically acceptable.

The medicament for reducing side effects of adrenocortical hormones of the present invention may contain one species of the present compound or two or more of its species in combination, according to a given purpose and need.

As it has very low toxicity and thus is highly safe, the present compound for the medicament for reducing side effects of adrenocortical hormones of the present invention can be used advantageously for the purpose of the present invention. [For example, a potassium salt of phosphodiester of L-ascorbic acid and DL-α-tocopherol (a compound wherein both $R_1$ and $R_2$ denote methyl, hereinafter referred to as "EPC-K"), a representative species of the present compound, has $LD_{50}$ values of over 5 g/kg (rat), p.o., and over 100 mg/kg (rat), i.v.]

The medicament for reducing side effects of adrenocortical hormones of the present invention may contain further ingredients having other pharmacological effects insofar as they does not contradict the purpose of the present invention.

The medicament for reducing side effects of adrenocortical hormones of the present invention may be used either orally or parenterally (e.g., by intravenous injection, subcutaneous injection, intramuscular injection, or intravenous drip). As for pharmaceutical preparation forms, it may be formed either into solid preparations including tablets, granules, powders, capsules and ointment, or into liquid preparations including injections, oral liquid preparations and eye drops, by known methods. For those preparations, conventional additives may be employed such as excipients, binders, disintegrants, dispersing agents, resorption enhancers, buffering agents, surfactants, solubilizers, preservatives, emulsifiers, isotonizers, stabilizers, pH adjusting agents and the like.

The medicament for reducing side effects of adrenocortical hormones of the present invention may be a pharmaceutical preparation comprising a mixture of an adrenocortical hormone and the present compound, or the respective components may be administered separately. The concentration of the adrenocortical hormone and the present compound in the mixture preparation is usually about 0.001%–about 1%, preferably about 0.01% to–about 0.5% for the adrenocortical hormone and about 1–about 100 times (weight ratio), preferably about 1–about 50 times (weight ratio) the amount thereof for the present compound, although it may vary in accordance with the species of the present compound and the specific adrenocortical hormone employed as well as with the form of the preparation. When an adrenocortical hormone and the present compound is administered separately, the dose for the present compound is about 1 mg–about 100 mg, preferably about 1 mg–about 50 mg per 1 mg of an adrenocortical hormone, although it may vary in accordance with the species of the present compound and the specific adrenocortical hormone employed, as well as with the age, body weight, sex, symptoms to be addressed and the form of the preparation. The present compound is administered at doses of about 0.5–about 200 mg, preferably about 2–about 50 mg per day for adult in the case of injections, at doses of about 5–about 2000 mg, preferably about 20–about 500 mg at one time, which is repeated several times a day for adult in the case of oral preparations, or in several drops at one time, which is repeated several times a day for adult in the case of eye drops whose concentration is about 0.01 W/V %–about 0.5 W/V %, or is applied several times a day in the case of ointment whose concentration is about 0.01 W/W %–about 5 W/W %.

BEST MODE FOR CARRYING OUT THE INVENTION

The present invention is described in further detail below with reference to examples and preparation examples. It should be noted, however, that the present invention is not limited by those examples.

EXAMPLE 1

Effect of the Present Compound to Reduce Side Effects of an Adrenocortical Hormone A test was carried out to examine the effect of the present compound to reduce side effects of an adrenocortical hormone.

(Test materials)
  0.012% betamethasone valerate (dissolved in methanol).
  0.012% betamethasone valerate +0.5% EPC-K (dissolved in methanol).

(Test method)
  10-week old female HR-1 hairless mice purchased from SLC Japan were used for the test. One hundred μl of the test materials were applied to the respective mice on the whole area of their back skin. This procedure was repeated once a day for two weeks, and then the body weight and the weight of the thymus and the spleen were determined.

(Results)
  Tables 1–3 show the rates of body weight increase and the weight of the thymus and the spleen determined two weeks after the application of the test materials.

TABLE 1

Rate of body weight increase

| Test materials | Rate (%) of body weight increase |
|---|---|
| 0.012% Betamethasone valerate | −7.4 ± 2.2 |
| 0.012% Betamethasone valerate + 0.5% EPC-K | −4.4 ± 2.3 |
| Normal (no application) | −1.0 ± 2.6 |

The figures indicate mean ± S.D. (n = 6–7).

TABLE 2

Organ weight (thymus)

| Test materials | Thymus (mg) |
|---|---|
| 0.012% Betamethasone valerate | 10.1 ± 2.4 |
| 0.012% Betamethasone valerate + 0.5% EPC-K | 20.3 ± 4.3*[2] |
| Normal (no application) | 23.9 ± 9.9*[1] |

The figures indicate mean ± S.D. (n = 6–7).
Significant difference from 0.012% betamethasone valerate: *[1]; $p < 0.01$, *[2]; $p < 0.001$

TABLE 3

Organ weight (spleen)

| Test materials | Spleen (mg) |
|---|---|
| 0.012% Betamethasone valerate | 5.3 ± 0.7 |
| 0.012% Betamethasone valerate + 0.5% EPC-K | 6.0 ± 0.5*[1] |
| Normal (no application) | 6.6 ± 1.3 |

The figures indicate mean ± S.D. (n ± 6–7).
Significant difference from 0.012% betamethasone valerate *[1]; $p < 0.05$ As clearly shown in Tables 1–3, the body weight reduction and the atrophy of thymus and spleen were suppressed by EPC-K administered concurrently with betamethasone valerate, demonstrating the effect of EPC-K to reduce side effects of the steroid. Thus the present compound was found to be useful as a medicament for reducing the side effects of adrenocortical hormones.

Reference Example

Synergism of Effects of the Present Compound and an Adrenocortical Hormone (antiinflammatory effect)

A test was performed for examining antiinflammatory effect observed by concurrent use of the present compound and an adrenocortical hormone. In addition, dose-response test was carried out for the adrenocortical hormone.
(Test materials)
  0.012% betamethasone valerate (dissolved in methanol).
  0.5% EPC-K (dissolved in methanol).
  0.012% betamethasone valerate +0.5% EPC-K (dissolved in methanol).
(Test method)
  10-week old male ICR mice purchased from SLC Japan were used for the test. Twenty μl of croton oil (6%) dissolved in acetone was applied on the outer surface of the right auricles of the mice to induce edema. Fifteen minutes later, 20 μl of one of the test materials was applied to each of the right auricles.

Four hours after the application of the test materials, the thickness of the right auricles of the mice were measured using a dial thickness gauge and edema rates were determined by comparing their thickness with that before induction.

(Results)

The results are shown in Tables 4–5.

TABLE 4

Synergism of the effects of the present compound and betamethasone valerate

| Test materials | Edema rate(%) | Inhibition rate(%) |
|---|---|---|
| Methanol | 116.1 ± 23.3 | — |
| 0.5% EPC-K | 109.1 ± 26.3 | 6.0 |
| 0.012% Betamethasone valerate | 87.3 ± 21.7 | 27.9 |
| 0.012% Betamethasone valerate + 0.5% EPC-K | 55.5 ± 20.4* | 52.2 |

The figures indicate mean ± S.D. (n = 23–27).
Significant difference from 0.012% betamethasone valerate or 0.5% EPC-K: *[1]; $p < 0.0.001$

TABLE 5

Dose-response test of betamethasone valerate

| Test materials | Edema rate(%) | Inhibition rate(%) |
|---|---|---|
| Methanol | 138.8 ± 18.5 | — |
| 0.012% Betamethasone valerate | 101.6 ± 15.3 | 26.8 |
| 0.040% Betamethasone valerate | 86.5 ± 30.3 | 37.7 |
| 0.12% Betamethasone valerate | 52.8 ± 13.3 | 62.0 |

The figures indicate mean ± S.D. (n = 8–9).

As clearly shown in Table 4, the concurrent use of the present compound and the steroid exhibited synergism of the effects compared with the results of their single use.

Based on the result of the dose-response test (Table 5), a calculation revealed that 0.088% of betamethasone valerate would give an effect comparable to the effect obtained by 0.012% betamethasone valerate plus 0.5% EPC-K.

| [Preparation Example 1] | Oral tablets |
|---|---|
| EPC-K | 100 mg |
| Lactose | 75 mg |
| Starch | 20 mg |
| Polyethylene glycol 6000 | 5 mg |

The above components are admixed by a conventional method to form a tablet. Sugar coating may be applied as needed.

| [Preparation Example 2] | Injection |
|---|---|
| EPC-K | 200 mg |
| Mannitol | 5.0 g |
| 1N Sodium hydroxide | q.s. |
| Distilled water | to 100 ml |
|  | pH 6.5 |

The above component are admixed to dissolve by a conventional method and the solution is aseptically filtered. The filtrate is aseptically introduced 5-ml each into glass ampoules, which then are heat-sealed to provide an injection.

| [Preparation Example 3] | Ointment |
|---|---|
| Hydrocortisone | 100 mg |
| EPC-K | 1.0 g |
| Hydrophilic ointment | to 100 g |

The ointment is made by a conventional method.

| [Preparation Example] | Eye drops |
|---|---|
| Sodium dexamethasone meta-sulfobenzoate | 10 mg |
| EPC-K | 0.2 g |
| Glycerol | 2.6 g |
| Methyl p-benzoate | 0.14 g |
| Propyl p-benzoate | 0.16 g |
| Sodium hydrogen phosphate | 0.1 g |
| Acetic acid | q.s. |
| Distilled water | to 100 ml |
|  | pH 6.5 |

The eye drops is made by a conventional method.

INDUSTRIAL APPLICABILITY

The pharmaceutical preparations of the present invention is useful as medicaments for reducing side effects of adrenocortical hormones, for they can directly and remarkably reduce the side effects of adrenocortical hormones without requiring reduction of their doses.

What is claimed is:

1. A method for reducing side effects caused by an adrenocortical hormone in a patient treated therewith, which method comprises administering to the patient in need thereof a phosphodiester compound of the following formula to a pharmacologically acceptable salt thereof in an amount sufficient to reduce side effects caused by an adrenocortical hormone

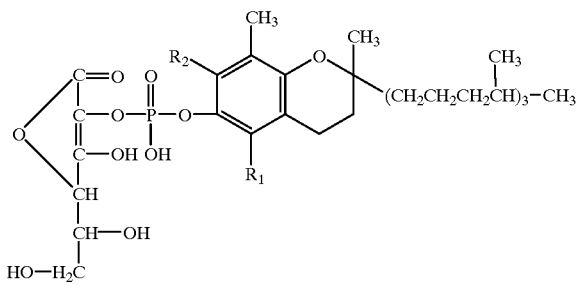

wherein $R_1$ and $R_2$ are the same or different and each denotes hydrogen or methyl.

2. The method according to claim 1, wherein the phosphodiester or a pharmacologically acceptable salt thereof and the adrenocortical hormone are administered in a ratio of 1–100 mg of the phosphodiester compound or a pharmacologically acceptable salt thereof to 1 mg of adrenocortical hormone.

3. The method according to claim 1, wherein the phosphodiester compound or a pharmacologically acceptable salt thereof is administered to treat side effects of an adrenocortical hormone selected from the group consisting of betamethasone valerate, hydrocortisone, sodium dexamethasone meta-sulfobenzoate, triamcinolone acetonide, alclometasone propionate, and fluocinolone acetonide.

4. The method according to claim 1, wherein the phosphodiester compound or a pharmacologically acceptable salt thereof is administered concurrently with the adrenocortical hormone.

5. A method for reducing side effects caused by an adrenocortical hormone in a patient treated therewith, which method comprises administering to the patient in need thereof a potassium salt of a phosphodiester compound of the following formula in an amount sufficient to reduce side effects caused by the adrenocortical hormone,

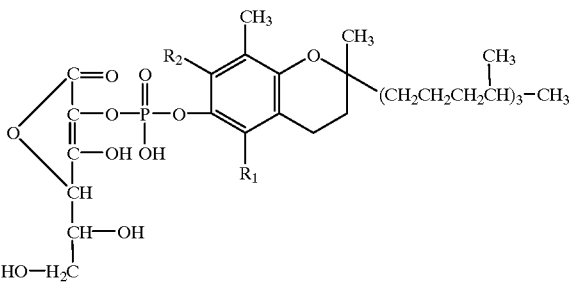

wherein each of $R_1$ and $R_2$ denotes methyl.

6. The method according to claim 5, wherein the potassium salt of a phosphodiester compound and the adrenocortical hormone are administered in a ratio of 1–100 mg of the potassium salt to 1 mg of the adrenocortical hormone.

7. The method according to claim 5, wherein the potassium salt of a phosphodiester compound is administered to treat side effects of an adrenocortical hormone selected from the group consisting of betamethasone valerate, hydrocortisone, sodium dexamethasone meta-sulfobenzoate, triamcinolone acetonide, alclometasone propionate, and fluocinolone acetonide.

8. The method according to claim 5, wherein the potassium salt of a phosphodiester compound is administered concurrently with the adrenocortical hormone.

* * * * *